US008803977B2

(12) United States Patent
Uchima et al.

(10) Patent No.: US 8,803,977 B2
(45) Date of Patent: Aug. 12, 2014

(54) METHOD FOR DETECTING DAMAGE TO A DECK OF A BRIDGE

(75) Inventors: Mitsuaki Uchima, Tokyo (JP); Hideaki Kurosu, Tokyo (JP); Chikakuni Maeda, Tokyo (JP); Tetsuji Yamagami, Osaka (JP); Shigeaki Tsukamoto, Osaka (JP)

(73) Assignee: Pasco Corporation, Tokyo (JP)

( * ) Notice: Subject to any disclaimer, the term of this patent is extended or adjusted under 35 U.S.C. 154(b) by 162 days.

(21) Appl. No.: 13/320,479

(22) PCT Filed: May 14, 2010

(86) PCT No.: PCT/JP2010/003292
§ 371 (c)(1),
(2), (4) Date: Jan. 27, 2012

(87) PCT Pub. No.: WO2010/131489
PCT Pub. Date: Nov. 18, 2010

(65) Prior Publication Data
US 2012/0120246 A1    May 17, 2012

(30) Foreign Application Priority Data
May 15, 2009  (JP) .................................. 2009-119329

(51) Int. Cl.
*H04N 5/33*    (2006.01)
*H04N 7/18*    (2006.01)

(52) U.S. Cl.
USPC ........................................ 348/164; 348/143

(58) Field of Classification Search
USPC .................................................. 348/164, 143
See application file for complete search history.

(56) References Cited

U.S. PATENT DOCUMENTS

| | | | | |
|---|---|---|---|---|
| 4,495,518 A * | 1/1985 | Sanoian | ........................ | 348/164 |
| 4,899,296 A * | 2/1990 | Khattak | .......................... | 702/40 |
| 5,201,582 A * | 4/1993 | Lesniak | .......................... | 374/45 |
| 6,119,526 A * | 9/2000 | Reigstad et al. | ................. | 73/803 |
| 6,422,741 B2 * | 7/2002 | Murphy et al. | .................... | 374/5 |
| 2005/0052742 A1 * | 3/2005 | Brinkmann et al. | .......... | 359/558 |

FOREIGN PATENT DOCUMENTS

| | | |
|---|---|---|
| JP | 3-20654 A | 1/1991 |
| JP | 2000-292388 A | 10/2000 |
| JP | 2003-247964 A | 9/2003 |
| JP | 2008-151809 A | 7/2008 |
| JP | 2008-232898 A | 10/2008 |

* cited by examiner

*Primary Examiner* — Chikaodili E Anyikire
(74) *Attorney, Agent, or Firm* — Birch, Stewart, Kolasch & Birch, LLP

(57) ABSTRACT

Provided is a method for detecting damage to a deck of a bridge, the method allowing detection work to be achieved with less labor and being capable of reducing the time and cost needed for the detection work. From a road-surface measuring vehicle running on pavement 3 on top of a steel-plate deck 1, a thermal infrared video of the surface of the pavement 3 is acquired by a thermal infrared video camera. Based on the thermal infrared video, troughs 4 of the steel-plate deck 1 are detected to grasp the structure of the steel-plate deck 1. Residence of water inside prescribed trough members 41 and sealing diaphragms 42 is detected from low-temperature regions R2 from among regions corresponding to troughs 4 in the thermal infrared video, and from rectangular low-temperature sections L2 that surround the regions R2. Through cracks are detected in deck plates 2 that correspond to troughs 4 in which residence of water has been detected.

1 Claim, 4 Drawing Sheets

METHOD FOR DETECTING DAMAGE TO A DECK OF A BRIDGE

TECHNICAL FIELD

The present invention relates to a method for detecting damage to a deck of a bridge by using a thermal infrared video captured from a surfaces side of pavement laid on a deck of a bridge, where the deck is positioned on a rear surface side of the pavement.

BACKGROUND ART

A bridge for roads such as viaducts of expressways (hereinafter, referred to as road bridge) is constituted, as a main structure, of bridge piers fixed on the ground, a main girder stretched between the bridge piers, a deck placed on the main girder, and pavement laid on the deck. Decks for road bridges, having a function of transferring a load of a vehicle running on the pavement to the bridge piers through the main girder, have been developed in various types, including RC decks formed from reinforced concrete, steel floor systems formed from steel material, composite decks formed from reinforced concrete and steel material, and the like.

To a deck of a road bridge, there may occur damage such as cracks and fissures due to repeated loads by running vehicles on the pavement. With such damage furthered, vicinities of damage are repeatedly displaced with load actions, causing the damage to be escalated with the result of occurrence of potholes, peeling or other damage at portions of the pavement located above the damage portion. Thus, damage to the deck causes damage to the pavement and moreover adversely affects traffic of vehicles, making it desirable to detect any damage to the deck in early stages. However, since the deck is covered with the pavement, it is difficult to detect any damage to the deck from the top surface side of the pavement. In many cases, detection of any damage to the deck is not achieved until damaged pavement is removed for repairing due to occurrence of potholes or the like in the pavement.

Conventionally proposed as a method for detecting damage to the deck of the road bridge in early stages is one using thermal videos of thermography (see Patent Literature 1). In this method for detecting damage to a deck, a pavement material of about 160° C. temperatures is laid on an upper side face of an RC deck, and temperature distributions shown on a lower side face derived from conduction of heat of the pavement material through the RC deck are acquired by a thermal infrared video camera from downward of the RC deck. With presence of cavities or voids as defective portions in the RC deck, temperature conduction is inhibited, so that surface temperatures of sites lower than the defective portions are shown as low-temperature regions as compared with sound portions. Accordingly, it is considered that presence of defective portions in the deck can be detected by extracting low-temperature regions in the lower side face of the deck.

Patent Literature 1: Japanese Unexamined Patent Application Publication No. 2003-247964

DISCLOSURE OF THE INVENTION

Problems to be Solved by the Invention

However, in the method for detecting damage to a deck of a bridge as described in PTL1, because of the need for capturing videos of the lower side face from downward of the deck with a thermal infrared video camera, there is a problem that the work of video capturing becomes difficult to achieve when other structures or railways or rivers and streams or the like are present downward of the road bridge. Therefore, in doing detection of damage to the deck with a long-distance elevated line targeted, time and labor for the detection work may be increased, leading to more time and cost. Further, since the method for detecting damage to a deck of a bridge involves video capturing of temperature distributions of the lower side face from downward of the deck, support members placed on the lower side of the deck make obstacles so as to make it difficult to grasp a whole temperature distribution of the deck, causing a problem that there are portions of the deck where the damage detection cannot be achieved.

Also, the method for detecting damage to a deck of a bridge as described in PTL1 involves a need for heating the deck to about 160° C. with a pavement material, occasions for performing damage detection of the deck are limited to cases in which the laying construction for the pavement is executed, posing a problem that the damage detection of the deck cannot be fulfilled with high degrees of freedom. Further, since the laying construction of the pavement is involved in doing damage detection of the deck, traffic control for the road is necessitated, posing another problem that the road traffic is largely affected.

Accordingly, an object of the present invention is to provide a method for detecting damage to a deck of a bridge which allows detection work to be achieved with less labor so that time and cost required for the detection work can be reduced. Another object of the invention is to provide a method for detecting damage to a deck of a bridge which makes it possible to achieve damage detection over the whole deck. A further object of the invention is to provide a method for detecting damage to a deck of a bridge which is free from a need for executing the method along with any other construction work and which can be executed at any arbitrary timing with a high degree of freedom. Still another object of the invention is to provide a method for detecting damage to a deck of a bridge which is free from a need for traffic control for the road so that the traffic control is less affected.

Solution to Problems

In order to solve the problems, a method for detecting damage to a deck of a bridge according to the present invention comprises:

a member detection step for, based on a thermal infrared video of a surface of pavement captured from the surface side of the pavement, detecting structural members of a deck positioned on a rear surface side of the pavement to support the pavement;

a residence-of-water detection step for, based on a temperature distribution pattern appearing on the surface of the pavement in association with the detected structural members of the deck, detecting residence of water inside the deck or on the surface of the deck; and a damage detection step for, based on detected residence of water, detecting damage to the structural members of the deck.

With this method for detecting damage to a deck of a bridge, based on the thermal infrared video of the surface of pavement captured from the surface side of the pavement, structural members of the deck positioned on the rear surface side of the pavement to support the pavement are detected. Based on a temperature distribution pattern appearing on the surface of the pavement in association with the detected structural members of the deck, residence of water inside the deck or on the surface of the deck is detected. For example, in a case where a region defined by detected specified structural members locally has a temperature difference from the other regions defined by the same kind of structural members, it can be decided that water is residing in the region defined by the specified structural members, on the ground that water is higher in heat capacity than concrete or iron and the like constituting the deck. Damage to the structural members of the deck is detected based on the detected residence of water. For example, it is detected that damage is present at a member which is defined by the specified structural members and which is positioned upward of the region where residence of water has been detected.

According to the method for detecting damage to a deck of a bridge with the above constitution, the thermal infrared video is captured from the surface side of the pavement. Therefore, for acquiring the thermal infrared videos, the video capturing work can be carried out easily without being affected by a state under the bridge even if some other structure, railway, or river and stream is present under the bridge. Thus, than in conventional methods in which the lower side surface of the deck is video-captured from its downward, time and labor for the damage detection work of the deck can be reduced, so that time and cost required for the work can be reduced. Also, since the thermal infrared videos are captured from the top surface side of the pavement, there never occur deficient portions due to obstacles of the support members as in the thermal infrared videos captured from the lower side surface of the deck. Accordingly, damage detection over the generally entirety of the deck can be achieved. Further, since the thermal infrared video is a motion video, a relatively long zone of the road can be captured in a relatively short time. Thus, the efficiency of the damage detection work of the deck can be enhanced.

Also according to the method for detecting damage to a deck of a bridge with the above constitution, the pavement of which a surface temperature distribution should be acquired as a thermal infrared video does not need to be heated by the pavement material or the like as in the conventional cases. That is, the method for detecting damage to a deck of a bridge in this invention is capable of sensing a temperature distribution generated in the pavement by spontaneous heating due to sunlight and discriminating temperature differences to thereby achieve damage detection of the deck. Therefore, the timing of damage detection of the deck is not limited to that of the laying construction of the pavement as in the conventional cases, and the damage detection of the deck can be carried out at high degrees of freedom. Further, since there is no need for heating the deck in advance with the pavement material or other heating mediums, the damage detection work of the deck can be achieved easily. Also, since there is no need for performing the laying construction of the pavement in executing the damage detection of the deck unlike the conventional cases, there is no need for traffic control over the road, so that influences given to the road traffic can be lessened.

The method for detecting damage to a deck of a bridge in this invention is not to directly detect the damage by thermal infrared videos, but to first detect residence of water by thermal infrared videos with attention focused on the correlation between prescribed members and residence of water to thereby detect any damage to the members. Thus, by detecting the damage to the members via residence of water, even if a member is positioned on the rear surface side of the pavement, damage detection of the member can be achieved with more simple detection work and with relatively less working time and cost than in the conventional cases.

In the method for detecting damage to a deck of a bridge according to one embodiment, the thermal infrared video is captured from a vehicle running on the pavement.

According to this embodiment, since the thermal infrared video is captured from the vehicle running on the pavement, there is no need for traffic control over the road on the pavement in spite of the video capturing from the surface side of the pavement. Thus, this damage detection method for the deck can lessen influences given to the road traffic during the execution of damage detection.

In the method for detecting damage to a deck of a bridge according to one embodiment, the thermal infrared video is captured by an indium antimony quantum type thermal infrared video camera.

According to this embodiment, by using an indium antimony quantum type thermal infrared video camera for capturing of thermal infrared videos, for example, it becomes possible to perform the video capturing from a vehicle running at a speed of 60 km to 100 km per hour with the indium antimony quantum type thermal infrared video camera mounted on the vehicle to acquire a clear thermal infrared video of the surface of the pavement. Therefore, video capturing of the thermal infrared videos can be achieved without incurring traffic jam of the road on the pavement, which is the target of video capturing. As a result, the damage detection work of the deck can be achieved with substantially no influences given to the road traffic.

In the method for detecting damage to a deck of a bridge according to one embodiment, the deck is a steel-plate deck having a steel-made deck plate for supporting the rear surface of the pavement, and steel-made troughs fixed on a lower side of the deck plate, the member detection step is to detect joint portions between the deck plate and the troughs based on a thermal infrared video of the surface of the pavement captured from the vehicle running on the pavement, the residence-of-water detection step is to detect, out of regions between neighboring ones of the detected joint portions of the deck plate and the troughs, a region having a temperature difference from the other regions as a region where residence of water has occurred, and wherein the damage detection step is to detect occurrence of a through crack at a portion of the deck plate corresponding to the region where residence of water has occurred.

According to this embodiment, with respect to the steel-plate deck having a steel-made deck plate and troughs, at the member detection step, joint portions between the deck plate and the troughs are detected based on a thermal infrared video of the surface of the pavement captured from the vehicle running on the pavement. At the residence-of-water detection step, out of regions between neighboring ones of the detected joint portions of the deck plate and the troughs, a region having a temperature difference from the other regions is detected as a region where residence of water has occurred. At the damage detection step, occurrence of a through crack is detected at a portion of the deck plate corresponding to the region where residence of water has occurred. Thus, based on the thermal infrared video obtained by capturing the surface of the pavement from the surface side of the pavement, the structure of the steel-plate deck on the rear side of the pavement is grasped, and residence of water in the region defined by the grasped structure is detected, by which any through crack of the deck plate of the steel-plate deck can be detected effectively. It is noted that the troughs constituting the steel-plate deck refer to members having a gutter shape and fitted to the lower side face of the deck plate.

A method for detecting damage to a deck of a bridge according to another aspect of the invention comprises:

a member temperature-distribution detection step for, based on a thermal infrared video of a surface of pavement captured from the surface side of the pavement, detecting a temperature distribution due to structural members of a deck positioned on a rear surface side of the pavement to support the pavement;

an air-layer and residence-of-water detection step for, based on a temperature distribution pattern due to the detected structural members of the deck, detecting presence of air or residence of water inside the deck or on the surface of the deck; and a damage detection step for, based on detected presence of air or residence of water, detecting damage to the structural members of the deck.

With this constitution, based on a thermal infrared video of the surface of the pavement captured from the surface side of the pavement, a temperature distribution due to structural members of the deck positioned on the rear surface side of the pavement to support the pavement are detected. Based on a temperature distribution pattern appearing on the surface of the pavement due to the detected structural members of the deck, presence of air or residence of water inside the deck or on the surface of the deck is detected. For example, in a case where a detected specified region locally has a temperature difference from the other regions, presence of air or residence of water in the specified region can be decided on the ground that water is higher in heat capacity than concrete or iron and the like constituting the deck while air is lower in heat capacity than concrete or iron and the like. Damage to the structural members of the deck is detected based on the detected presence of air or the residence of water. For example, it is detected that damage is present at a member which is positioned in the specified region.

Also according to the method for detecting damage to a deck of a bridge with the above constitution, there is no need for heating the pavement in advance with the pavement material or the like, unlike the conventional cases, and a temperature distribution caused in the pavement by spontaneous heating with the solar light is sensed, and temperature differences are discriminated to perform damage detection of the deck. Therefore, the damage detection of the deck can be achieved with a high degree of freedom. Further, since there is no need for heating the deck with the pavement material or other heating mediums in advance, the damage detection work of the deck can be achieved easily. Also, since there is no need for performing the laying construction of the pavement in executing the damage detection of the deck unlike the conventional cases, there is no need for traffic control over the road, so that influences given to the road traffic can be lessened.

In the method for detecting damage to a deck of a bridge according to one embodiment, the deck is a reinforced concrete deck having reinforcing steels and concretes to support a rear surface of the pavement, the member temperature-distribution detection step is to detect a region where a temperature difference from the other regions of the concretes has occurred based on a thermal infrared video of the surface of the pavement captured from a vehicle running on the pavement, the air-layer and residence-of-water detection step is to detect, based on a value of the temperature difference of a detected region from the other regions, an air layer or residence of water in the region of the concretes, and wherein the damage detection step is to detect a void, a crack or deterioration at a concrete portion where an air layer or residence of water has occurred.

According to this embodiment, with respect to the reinforced concrete deck having reinforcing steels and concretes, at the member temperature-distribution detection step, a region having occurrence of a temperature difference from the other regions of the concretes is detected based on a thermal infrared video of the surface of pavement captured from the vehicle running on pavement. At the air-layer and residence-of-water detection step, based on a value of the temperature difference of the detected region from the other regions, occurrence of an air layer or water residing in the region of the concrete is detected. At the damage detection step, occurrence of a crack is detected at a portion of the concrete corresponding to the region having occurrence of the air layer or water residing. Thus, based on the thermal infrared video obtained by video capturing of the surface of the pavement from the surface side of the pavement, a temperature distribution of the concrete deck on the rear side of the pavement is grasped, and an air layer or water residing is detected based on the grasped temperature distribution, by which cracks of the concrete of the concrete deck can be detected effectively.

Effects of the Invention

According to this invention, the structure of the deck on the rear surface side of the pavement can be grasped indirectly based on the thermal infrared video of the surface of the pavement captured from the surface side of the pavement. By detecting residence of water corresponding to this structure, damage to the deck such as through cracks or the like of the deck plate can be detected.

DETAILED DESCRIPTION OF THE PREFERRED EMBODIMENTS

Hereinbelow, an embodiment of the present invention will be described in detail with reference to the accompanying drawings.

Figure 1:
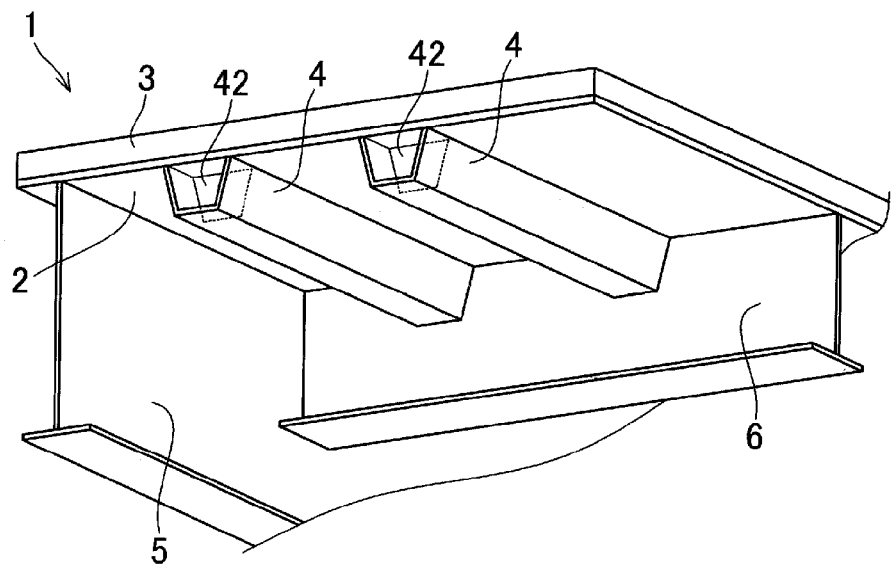
FIG. 1 is a view showing a deck made from steel to which a damage detection method according to an embodiment of the invention is applied.

FIG. 1 is a view showing an aspect of a deck made from steel, as observed from below, as a deck to which a deck-damage detection method according to this embodiment is applied. This steel-plate deck 1 has a deck plate 2, and a pavement 3 laid on a top surface of the deck plate 2. On a lower surface of the deck plate 2, provided as reinforcing members are troughs 4 each having a U-shaped cross section and extending along a bridge-axis direction, longitudinal ribs 5 extending parallel to the troughs 4 and having an I-type cross section, and lateral ribs 6 extending along a direction orthogonal to the bridge axis. The deck plate 2, the troughs 4, the longitudinal ribs 5 and the lateral ribs 6 are in all cases formed from steel material. The troughs 4, the longitudinal ribs 5 and the lateral ribs 6 are fixed to the deck plate 2 by welding. In a weld zone between the troughs 4 and the deck plate 2, a bead 21 is formed as shown in the sectional view of FIG. 2.

The pavement 3 is formed from asphalt. Instead of being formed only from asphalt, the pavement 3 may be formed at least partly from concrete or resin.

This steel-plate deck 1, which is used for viaducts of urban expressways, is supported by unshown bridge piers.

Figure 2:
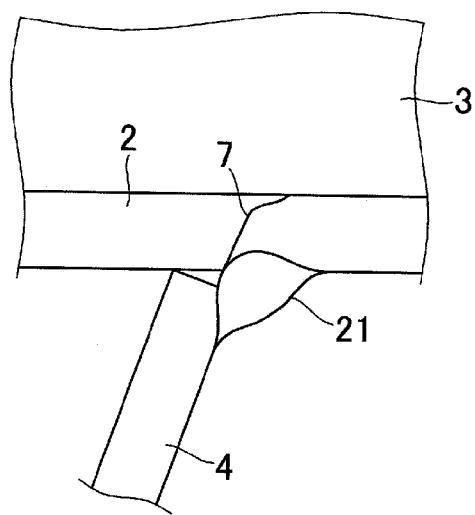
FIG. 2 is a partial cross-sectional view showing a crack that occurs in a weld zone between a trough and a deck plate.

This type of steel-plate deck 1 frequently undergoes loads of vehicles that run on the pavement 3, so that a through crack 7 occurs to the deck plate 2, with the weld zone of the deck plate 2 and the troughs 4 taken as a starting point, as shown in FIG. 2. The through crack 7 of the deck plate 2 in one case develops from an end edge of the bead 21 on an inner side of the troughs 4 as shown in FIG. 2, and in another case develops from an end edge of the bead 21 on an outer side of the troughs 4. In either case, vicinal portions of the through crack 7 in the deck plate 2 are displaced with passage of vehicles, so that large damage may occur to the vicinal portions of the through crack 7 in the pavement 3. Thus, damage to the pavement 3 is related to the through crack 7 and may be detrimental to safe running of vehicles, giving rise to a need for early finding and repair of the through crack 7 of the deck plate 2.

Under such circumstances as shown above, in this embodiment, the through crack 7 as damage to the deck plate 2 is detected by using thermal infrared videos for all the steel-plate decks 1 constituting specified road ways of urban expressways.

Figure 3:
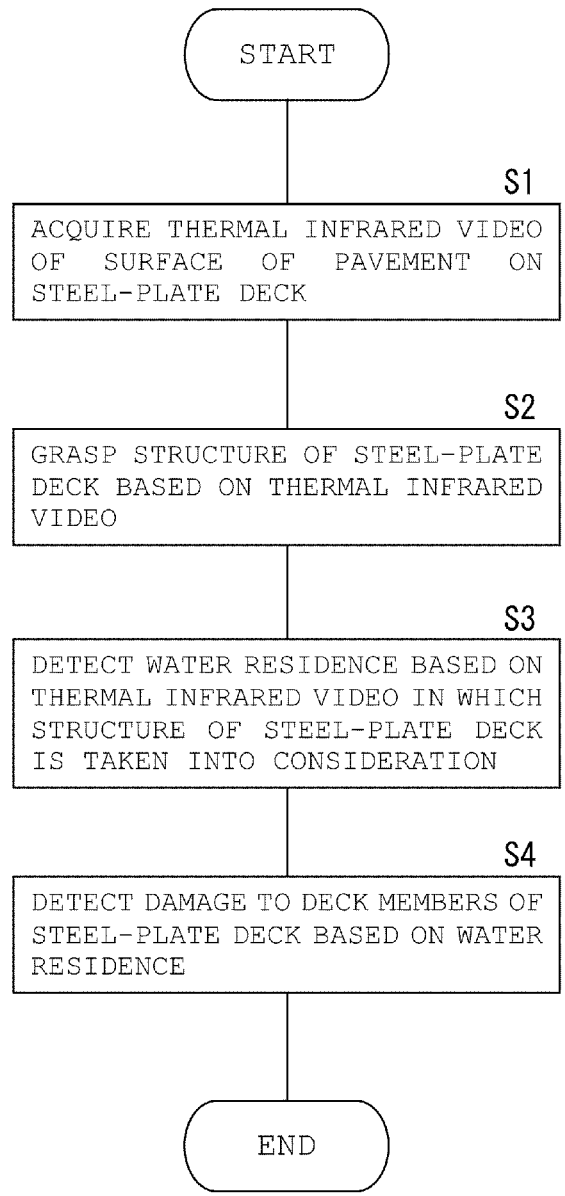
FIG. 3 is a flowchart showing processes of the method for detecting damage to a deck of a bridge according to the embodiment.

FIG. 3 is a flowchart showing processes of the method for detecting damage to a deck of a bridge according to the embodiment. As shown in the flowchart of FIG. 3, first, a thermal infrared video of the top surface of the pavement 3 on the steel-plate deck 1 is acquired (step S1). Based on this thermal infrared video, members of the steel-plate deck 1 are detected, by which its structure is grasped (step S2). Subsequently, based on the thermal infrared video and with considerations given to the grasped structure of the steel-plate deck 1, residence of water in the steel-plate deck 1 is detected (step S3). Thereafter, based on the detected residence of water, damage to the members of the steel-plate deck 1 is detected (step S4). Details of the individual steps will be described below.

(Step S1)

A thermal infrared video of the top surface of the pavement 3 on the steel-plate deck 1 is captured from a vehicle running on the pavement 3. In this vehicle, which is road-surface measuring vehicle fabricated by modifying a microbus or box-type commercial vehicle, a video capturing device with a thermal infrared video camera and a visible light video camera mounted thereon is provided on a roof of the front side portion in the running direction. The thermal infrared video camera, which is an indium antimony quantum type one, is higher in sensitivity than microbolometer type cameras or the like, and therefore can obtain thermal infrared videos with less blurs while moving at speeds of about 60 km to 100 km per hour. By the thermal infrared video camera, the surface of the pavement 3 in front of the road-surface measuring vehicle is video-captured at equal time intervals (e.g., 5 frames per second) or at equal distance intervals (e.g., 5 m intervals) to acquire thermal infrared videos, while the generally same range as the video-capturing range by the thermal infrared video camera is video-captured by the visible light video camera simultaneously. In the road-surface measuring vehicle, a GPS (Global Positioning System) antenna is provided, so that positional information received by the antenna is stored in a storage device in association with thermal infrared videos and visible light videos.

By the road-surface measuring vehicle, which is running over a viaduct of urban expressways that is the object of damage detection, thermal infrared videos of the pavement 3 are captured. In this process, since the thermal infrared videos are captured by a thermal infrared video camera of the indium antimony quantum type, the road-surface measuring vehicle is permitted to run at a speed of about 60 km or more per hour. Accordingly, while the viaduct remains opened to general vehicles, the video capturing can be achieved without applying traffic control on a driving lane for the road-surface measuring vehicle and yet no traffic jam is caused. As a result of this, the damage detection work of the steel-plate deck 1 can be carried out with substantially no influences given to the road traffic. In this embodiment, thermal infrared videos of the pavement 3 were captured during a period from 14:00 to 14:30, in which daily temperature comes to a maximum, so that temperature distributions of the surface of the pavement 3 at the time of a maximum bridge temperature as a whole were acquired.

(Step S2)

Figure 4:
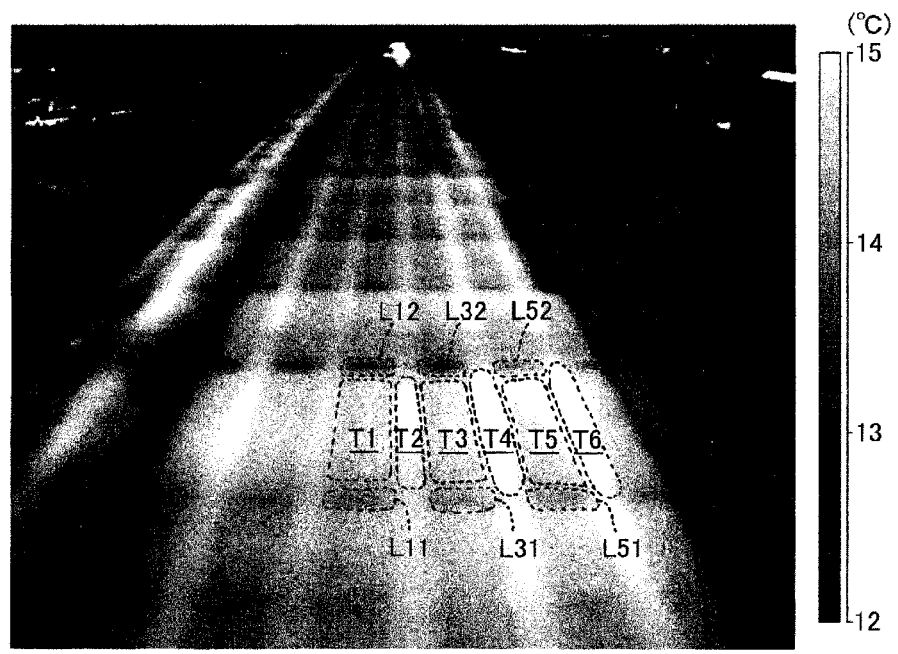
FIG. 4 is a view showing one frame of a thermal infrared video of pavement.

Based on the thermal infrared videos, the members of the steel-plate deck 1 are detected to grasp the structure. FIG. 4 is a view showing one frame of the thermal infrared videos captured from the running road-surface measuring vehicle. It is noted that a thermal infrared video is obtained as a color distribution chart in which temperature distributions of the surface of the pavement 3 are shown generally as a color gradation ranging from red to purple. Whereas a gradation scale representing correspondence between colors and temperatures is shown at an end of FIG. 4, FIG. 4 is shown only by brightness with the colors deleted. As shown in FIG. 4, placement regions of the troughs 4, which is a member of the steel-plate deck 1, are shown as high-temperature regions T2, T4, T6 on the surface of the pavement 3. On the other hand, inter-trough regions which are regions between neighboring ones of the troughs 4 and in which the lower side face of the deck plate 2 are exposed are shown as low-temperature regions T1, T3, T5 lower than the high-temperature regions T2, T4, T6. This is because air sealed within the troughs 4 is heated by sunbeams via the pavement 3 so as to be increased in temperature as compared with portions between neighboring troughs 4 in contact with outside air.

At longitudinal both ends of the low-temperature regions T1, T3, T5 showing the inter-trough regions, respectively, present are linear-shaped low-temperature portions L11, L12, L31, L32, L51, L52 which are of further lower temperatures. These low-temperature portions L11, L12, . . . show placement positions of the lateral ribs 6 placed along the lower side faces of the deck plate 2 and the troughs 4.

In the thermal infrared videos, for example as in FIG. 4, positions of the troughs 4 are shown as the high-temperature regions T2, T4, T6, and positions of the lateral ribs 6 are shown as the low-temperature portions L11, L12, . . . , thus allowing the structure of the steel-plate deck 1 to be grasped. Tables 1 and 2 list results of measurement performed on 80 samples, where temperatures of the high-temperature regions T2, T4, T6 and the low-temperature regions T1, T3, T5 were measured when the whole bridge reached a maximum temperature in a daily maximum temperature time zone under meteorological conditions of a daily maximum temperature of 14.8° C. and a fair weather. As can be understood from Tables 1 and 2, there is a temperature difference that the placement regions of the troughs 4 are 0.4° C. higher than regions between neighboring troughs 4 where the troughs 4 are not arrayed.

TABLE 1

| Reference No. | T2 | T4 | T6 |
|---|---|---|---|
| Region | Trough placement region | | |
| Temp. ± standard deviation (° C.) | 15.0 ± 0.1 | 15.2 ± 0.1 | 15.4 ± 0.1 |
| Average | | 15.2 | |

TABLE 2

| Reference No. | T1 | T3 | T5 |
|---|---|---|---|
| Region | Inter-trough region | | |
| Temp. ± standard deviation (° C.) | 14.6 ± 0.2 | 14.8 ± 0.1 | 14.9 ± 0.1 |
| Average | | 14.8 | |

Also, there arises a temperature difference that the low-temperature portions L11, L12, . . . are 1 to 1.5° C. lower than the high-temperature regions T2, T4, T6. In this way, based on the thermal infrared videos by video capturing of the surface of the pavement 3, the troughs 4 and the lateral ribs 6 that are the members of the steel-plate deck 1 present on the rear face side of the pavement 3 can be grasped, that is, the structure of the steel-plate deck 1 can be grasped.

(Step S3)

Figure 5:
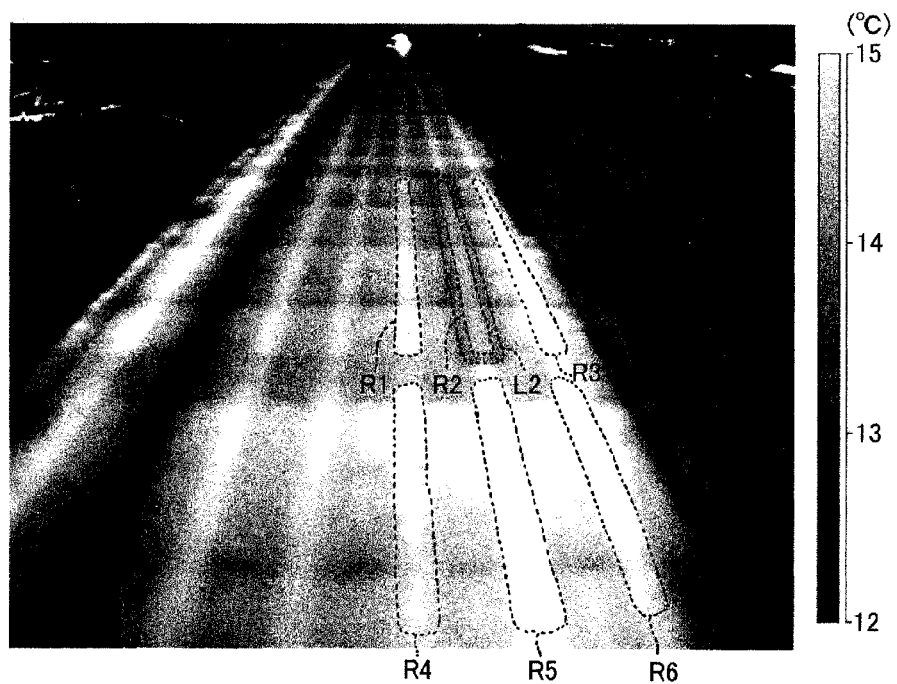
FIG. 5 is a view showing one frame of a thermal infrared video of the pavement in a region including water-stagnant portions of the deck.

Based on the structure of the steel-plate deck 1 grasped at step S2, residence of water in the members of the steel-plate deck 1 is detected. FIG. 5 shows one frame of thermal infrared videos of a water-residing pavement portion on the steel-plate deck 1, the steel-plate deck 1 having generally the same structure as that grasped in FIG. 4.

Figure 6:
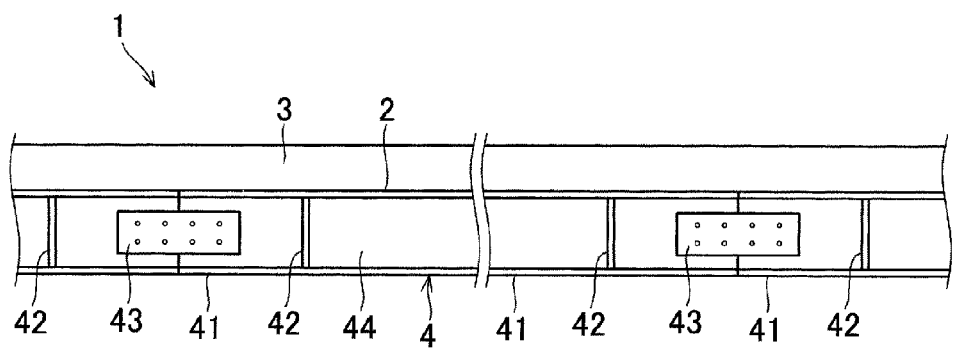
FIG. 6 is a longitudinal sectional view showing an internal structure of the trough.

FIG. 6, which is for explaining structural members of the steel-plate deck 1 shown in the thermal infrared video of FIG. 5, is a longitudinal sectional view showing an internal structure of the trough 4 of the steel-plate deck 1. As shown in FIG. 6, each of the troughs 4 is made up of a plurality of trough members 41, 41, . . . welded to the lower side face of the deck plate 2. The trough members 41 correspond to divided units, respectively, of the steel-plate deck 1 made in divisions for transportation's sake in manufacture of the steel-plate deck 1. In construction of the steel-plate deck 1, the divided units are carried in to a construction site and assembled together, and the trough members 41 are joined to joint plates 43 with bolts, by which the trough 4 are formed up. Near both ends of the trough members 41, sealing diaphragms 42 are provided for partitioning of joint portions. Between the sealing diaphragms 42 inside the trough members 41, their upper edges are welded to the deck plate 2 to provide a sealing, so that the base material is exposed with no rust-preventive treatment applied.

As shown in FIG. 5, out of regions R1, R2, R3, R4, R5, R6 corresponding to a plurality of troughs 4, a depthwise region R2 on the 2nd array as counted from the right end of an video-capture targeted lane toward the left is 1.3° C., at a maximum, lower in temperature than the other regions R1, R3, R4, R5. Further, according to FIG. 5, a rectangular frame-shaped low-temperature portion L2 is present so as to surround the low-temperature region R2. This low-temperature portion L2 is 0.6 to 0.8° C. lower in temperature than regions corresponding to the portions between neighboring troughs 4. This represent that air inside the trough 4 corresponding to the region R2 is lower in temperature than air inside the troughs 4 corresponding to the other regions R1, R3, R4, R5. It is also represented that the trough member 41 and the sealing diaphragm 42 corresponding to the region R2 are lower in temperature than the other trough members 41 and sealing diaphragms 42 as well as the deck plate 2.

Table 3 and 4 list results of measurement performed on 200 samples for the regions R1, R2, R3 and on 150 samples for the regions R4, R5, R6 in combination with in-trough states, where temperatures of the regions R1, R2, R3, R4, R5, R6 corresponding to the troughs 4 were measured under the same conditions as in Tables 1 and 2. It is noted that the regions R1 and R4, the regions R2 and R5, and the regions R3 and R6 are regions corresponding to identical troughs 4, respectively, the regions of each pair are partitioned by the sealing diaphragm 42.

TABLE 3

| Reference No. | R1 | R2 | R3 |
|---|---|---|---|
| In-trough state | No water residing | Water residing | No water residing |
| Temp. ± standard deviation (° C.) | 14.9 ± 0.2 | 14.4 ± 0.2 | 15.4 ± 0.3 |

TABLE 4

| Reference No. | R4 | R5 | R6 |
|---|---|---|---|
| In-trough state | No water residing | No water residing | No water residing |
| Temp. ± standard deviation (° C.) | 15.3 ± 0.2 | 15.7 ± 0.2 | 15.6 ± 0.3 |

In a case where the low-temperature region R2 corresponding to a trough 4 and the low-temperature portion L2 surrounding the region R2 are shown in the thermal infrared video of the pavement 3 as shown in FIG. 5, it can be decided that water that causes the temperature of air inside the trough 4 and the temperature of the trough 4 and the sealing diaphragm 42 to be lowered is present in a portion between the trough 4 and the sealing diaphragm 42 corresponding to the region R2. Thus, detecting a high-temperature region lower in temperature than the other high-temperature regions as well as a frame-shaped low-temperature region surrounding the high-temperature region in the thermal infrared video of the pavement 3 makes it possible to detect water residing in that region.

(Step S4)

Based on the residence of water detected at step S3, a through crack of members of the steel-plate deck 1 is detected. The trough 4 has its upper end welded to the lower side face of the deck plate 2, and the sealing diaphragm 42 in the trough 4 has its upper end edge welded to the deck plate 2 and its edges other than the upper end edge welded to the inner side face of the trough member 41. Accordingly, there occurs no water residing in the region sealed by the sealing diaphragm 42 in the trough 4. In this case, upon detection of residence of water in the trough 4 at step S3, it can be assumed that rainfall to the pavement 3 has intruded into the trough 4 through the through crack 7 of the deck plate 2. When a position corresponding to the region R2 of the trough 4 of FIG. 5 was actually examined, a through crack 7 was found out at a welding portion of the trough 4 of the deck plate 2. Like this, residence of water in the trough 4 welded to the lower side face of the deck plate 2 has a high correlation to the through crack 7 of the deck plate 2. Therefore, detecting the residence of water allows a through crack of the deck plate 2 to be detected.

When a through crack of the deck plate 2 is detected as shown above, positional information associated with a frame of a thermal infrared video is extracted, and a damage site is specifically determined based on the positional information, followed by performing repair work of the steel-plate deck 1. Since the residence of water within the trough 4 arises in a relatively short period from generation of a through crack in the deck plate 2, applying the detection method of this embodiment allows early detection and repair of the through crack to be achieved. As a result, it becomes possible to effectively prevent the possibility that the deck plate 2 is largely deformed due to the through crack and moreover the pavement incurs occurrence of large damage so as to adversely affect the road traffic, disadvantageously.

According to the method for detecting damage to a deck of a bridge in this embodiment, thermal infrared videos are captured by a thermal infrared video camera of a road-surface measuring vehicle running on the pavement 3. Therefore, for acquiring the thermal infrared videos, the video capturing work can be carried out easily without being affected by a state under the bridge even if some other structure, railway, or river and stream is present under the bridge. Thus, than in conventional methods in which the deck is video-captured from downward, time and labor for the damage detection work of the deck can be reduced, so that time and cost required for the work can be reduced. Also, since the thermal infrared videos are captured from the top surface side of the pavement 3 on the steel-plate deck 1, the whole surface of the pavement 3 can be video-captured. Accordingly, damage detection over the generally whole surface of the steel-plate deck 1 can be achieved without occurrence of inspection-deficiency portions due to obstacles of the support members or the like as in the cases in which video capturing of the deck is performed from its lower side face. Further, since the thermal infrared video is a video, a relatively long zone of the road can be captured in a relatively short time. Thus, the efficiency of the damage detection work of the steel-plate deck 1 can be enhanced.

Also according to this embodiment, since the thermal infrared video is captured from the road-surface measuring vehicle running on the pavement 3, there is no need for traffic control over the road on the pavement 3. Thus, influences given to the road traffic during the execution of damage detection of the steel-plate deck 1 can be lessened.

Also according to this embodiment, since temperature distributions of the surface of the pavement 3 due to spontaneous heating by sunbeams are video-captured by the thermal infrared video camera, there is no need for heating the deck before the video capturing as in the conventional cases. Therefore, the timing for performing the damage detection of the steel-plate deck 1 can be set at high degrees of freedom without being limited to that of the laying construction of pavement as in the conventional cases. Further, since there is no need for performing the laying construction of the pavement in executing the damage detection of the deck unlike the conventional cases, there is no need for traffic control over the road, so that influences given to the road traffic can be lessened.

Also according to this embodiment, since the indium antimony quantum type thermal infrared video camera is used for capturing of thermal infrared videos, thermal infrared videos of the surface of the pavement 3 can be captured with this camera mounted on the vehicle under a running at a speed of 60 km or more per hour. Therefore, video capturing of the thermal infrared videos can be achieved without incurring traffic jam of the road on the pavement 3, which is the target of video capturing. As a result, the damage detection work of the steel-plate deck 1 can be achieved with substantially no influences given to the road traffic.

In the embodiment described above, video capturing of the pavement 3 is done in a daily maximum temperature time zone, by which a temperature distribution of the pavement 3 at a time point when the temperature of the bridge as a whole reaches a maximum is acquired. However, the video capturing of the pavement 3 may also be performed at a time point when 3 to 4 hours have elapsed since a sunset, so that a temperature distribution of the pavement 3 for lowered temperatures of the bridge as a whole is acquired. In this case, in the thermal infrared video, placement regions of the troughs 4 appear as regions of temperatures lower than temperatures of the other regions between neighboring troughs 4. Further, troughs 4 with water residing appear as regions of higher temperatures than troughs 4 with no water residing, and the trough members 41 and the sealing diaphragms 42 surrounding water-residing regions appear as linear portions of even higher temperatures.

In this embodiment, residence of water in the members of the steel-plate deck 1 is detected by thermal infrared videos. However, residence of water on the top surface side of the deck plate 2 of the steel-plate deck 1 may also be detected.

In this embodiment, temperatures of individual structural members as well as temperature differences among those members to be represented as temperature distributions of the thermal infrared video are shown only as an example. There may occur temperature variations, temperature differences, and high-low relationships depending on the maximum temperature, weather, video capturing time zone, and so on in the video-capturing day of the thermal infrared video.

The above embodiment has been described on a case in which damage detection of the steel-plate deck 1 as a deck of a bridge is performed. Instead, damage detection of an RC deck as a deck of a bridge may also be performed. In the case where damage detection of an RC deck is performed, thermal infrared videos of the surface of the pavement are captured during a running of the same road-surface measuring vehicle as used in the above embodiment on the pavement laid on the RC deck. In the case where this thermal infrared video is acquired in the daytime at and after about 4 hour elapse since the sunrise, on condition that air is present with an air layer formed inside the RC deck or between the RC deck and the pavement, a region where this air is present appears as a higher-temperature region than regions where no air is present, in the thermal infrared video. Meanwhile, in a case where water is residing inside the RC deck or between the RC deck and the pavement, a region where water is residing appears as a lower-temperature region than regions where no water is residing. From these factors, when the presence of air or the residence of water is detected, there can be detected, in a concrete portion corresponding to a region of the above detection, a void or crack that causes an air layer and water residing, or deteriorations such as floating or honeycombs. Thus, based on a thermal infrared video obtained by capturing a video of the top surface of the pavement from the top surface side of the pavement, a temperature distribution of concretes of the RC deck positioned on the rear surface side of the pavement is grasped, and any air layer or water residing of a specified region is detected based on the temperature distribution. As a consequence of this, voids, cracks or deteriorations of concretes of the concrete deck can be detected effectively with less time and labor.

REFERENCE NUMERALS 1 steel-plate deck
2 deck plate
3 pavement 4 trough
5 longitudinal rib
6 lateral rib
7 through crack of deck plate

What is claimed is:

1. A method for detecting damage to a deck of a bridge, comprising:
- a member detection step for, based on a thermal infrared video of a surface of pavement that has temperature distribution generated by spontaneous heating due to sunlight captured from the surface side of the pavement, detecting structural members of a deck positioned on a rear surface side of the pavement to support the pavement;
- a residence-of-water detection step for, based on a temperature distribution pattern appearing on the surface of the pavement in association with the detected structural members of the deck, detecting residence of water inside the deck or on the surface of the deck; and
- a damage detection step for, based on detected residence of water, detecting damage to the structural members of the deck, wherein the deck is a steel-plate deck having a steel-made deck plate for supporting the rear surface of the pavement, and steel-made troughs fixed on a lower side of the deck plate, the member detection step is to detect joint portions between the deck plate and the troughs based on a thermal infrared video of the surface of the pavement captured from the vehicle running on the pavement, the residence-of-water detection step is to detect, out of regions between neighboring ones of the detected joint portions of the deck plate and the troughs, a region having a temperature difference from the other regions as a region where residence of water has occurred, and wherein the damage detection step is to detect occurrence of a through crack at a portion of the deck plate corresponding to the region where residence of water has occurred.

* * * * *